(12) United States Patent
Goodson, IV et al.

(10) Patent No.: US 8,333,797 B2
(45) Date of Patent: Dec. 18, 2012

(54) STENT-GRAFT DELIVERY SYSTEM

(75) Inventors: Harry Goodson, IV, Fremont, CA (US); Jeff Elkins, Novato, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 407 days.

(21) Appl. No.: 12/564,689

(22) Filed: Sep. 22, 2009

(65) Prior Publication Data

US 2010/0010617 A1      Jan. 14, 2010

Related U.S. Application Data (62) Division of application No. 10/351,055, filed on Jan. 24, 2003, now Pat. No. 7,611,528.

(51) Int. Cl.
*A61F 2/06* (2006.01)

(52) U.S. Cl. ............ 623/1.11; 623/1.13; 623/1.23

(58) Field of Classification Search .............. 623/1.11, 623/1.23, 1.13
See application file for complete search history.

(56) References Cited

U.S. PATENT DOCUMENTS

| | | | |
|---|---|---|---|
| 4,990,151 A | 2/1991 | Wallsten | |
| 5,387,235 A | 2/1995 | Chuter | |
| 5,415,664 A * | 5/1995 | Pinchuk | 623/1.11 |
| 5,456,713 A | 10/1995 | Chuter | |
| 5,480,423 A | 1/1996 | Ravenscroft et al. | |
| 5,562,726 A | 10/1996 | Chuter | |
| 5,693,084 A | 12/1997 | Chuter | |
| 5,733,325 A | 3/1998 | Robinson et al. | |
| 5,755,777 A | 5/1998 | Chuter | |
| 5,776,142 A | 7/1998 | Gunderson | |
| 5,824,041 A * | 10/1998 | Lenker et al. | 606/195 |
| 5,824,058 A | 10/1998 | Ravenscroft et al. | |
| 5,902,334 A * | 5/1999 | Dwyer et al. | 606/194 |
| 5,935,161 A | 8/1999 | Robinson et al. | |
| 6,077,297 A | 6/2000 | Robinson et al. | |
| 6,143,021 A | 11/2000 | Staehle | |
| 6,251,132 B1 | 6/2001 | Ravenscroft et al. | |
| 6,395,017 B1 | 5/2002 | Dwyer et al. | |
| 6,468,298 B1 | 10/2002 | Pelton | |
| 6,524,335 B1 * | 2/2003 | Hartley et al. | 623/1.13 |
| 6,582,460 B1 | 6/2003 | Cryer | |
| 6,656,212 B2 | 12/2003 | Ravenscroft et al. | |
| 6,676,692 B2 | 1/2004 | Rabkin et al. | |
| 7,264,632 B2 * | 9/2007 | Wright et al. | 623/1.12 |
| 7,611,528 B2 * | 11/2009 | Goodson et al. | 623/1.11 |
| 7,803,177 B2 * | 9/2010 | Hartley et al. | 623/1.11 |
| 7,815,671 B2 * | 10/2010 | Wright et al. | 623/1.12 |
| 2003/0233140 A1 | 12/2003 | Hartley et al. | |
| 2004/0093063 A1 * | 5/2004 | Wright et al. | 623/1.12 |
| 2004/0148008 A1 | 7/2004 | Goodson et al. | |

FOREIGN PATENT DOCUMENTS

| | | |
|---|---|---|
| EP | 1097728 | 5/2001 |
| EP | 1212989 | 6/2002 |
| FR | 002779939 | 6/1998 |
| WO | WO96/18361 | 6/1996 |
| WO | WO97/12563 | 4/1997 |
| WO | WO98/53761 | 12/1998 |

* cited by examiner

*Primary Examiner* — Darwin Erezo (57) ABSTRACT

A method of delivering a stent-graft includes mounting the stent-graft on a pushrod; radially constraining the stent-graft within a sheath; securing a crown portion of the stent-graft to the pushrod with a retainer structure of a stent-graft retainment system; retracting the sheath to expose the crown portion of the stent-graft; and further retracting the sheath to cause the retainer structure to release the crown portion from the pushrod thus deploying the stent-graft. The retainer structure releases the stent-graft automatically as a result of the retraction of the sheath.

6 Claims, 6 Drawing Sheets

STENT-GRAFT DELIVERY SYSTEM

This application claims the benefit and priority of U.S. application Ser. No. 10/351,055 filed Jan. 24, 2003, now U.S. Pat. No. 7,611,528.

BACKGROUND OF THE INVENTION

1. Field of the Invention

The present invention relates to an intra-vascular device and method. More particularly, the present invention relates to a device for deployment of a stent-graft for treatment of intra-vascular aneurysms.

2. Description of the Related Art

In stent-graft deployment systems, a self-expanding stent-graft is restrained within a sheath. After placement of the stent-graft at the desired location via fluoroscopic guidance, the physician retracts the sheath to deploy the stent-graft, i.e., to expose the stent-graft and allow it to self-expand.

However, prior to deployment, the compressed stent-graft tends to press outwards on the inner surface of the sheath because of its high radial force, self-expanding design. As a result, significant deployment force is required to retract the sheath to deploy the stent-graft.

This significant deployment force puts significant stress on the stent-graft, which can result in damage or destruction of the stent-graft during deployment. Further, this significant deployment force places significant stress on the delivery system, which can lead to component failure of the delivery system.

SUMMARY OF THE INVENTION

In one embodiment according to the present invention, a method of delivering a stent-graft includes mounting the stent-graft on a pushrod; radially constraining the stent-graft within a sheath; securing a crown portion of the stent-graft to the pushrod with a retainer structure of a stent-graft retainment system; retracting the sheath to expose the crown portion of the stent-graft; and further retracting the sheath to cause the retainer structure to release the crown portion from the pushrod thus deploying the stent-graft.

The retainer structure releases the stent-graft automatically as a result of the retraction of the sheath. Thus, in accordance with this embodiment of the present invention, exposure of the crown portion of the stent-graft by retraction of the sheath is followed by release of the crown portion of the stent-graft by the retainer structure without requiring any additional manipulations by the physician compared to a conventional stent-graft delivery system.

Since the retainer structure holds the crown portion against the pushrod during initial retraction of the sheath, the normal force exerted by the crown portion of the stent-graft against the sheath is minimized. Since this normal force is minimized, graft-to-sheath friction is minimized thus minimizing the stent-graft deployment (sheath retraction) force.

By minimizing the deployment force, the stress on the stent-graft is minimized thus minimizing the possibility of damaging the stent-graft during deployment. Further, by minimizing the deployment force, the stress on the stent-graft delivery system is minimized thus also minimizing the possibility of damaging the stent-graft delivery system during deployment of the stent-graft.

In another embodiment according to the present invention, a stent-graft delivery system includes: a pushrod having a lumen and a trigger aperture; a stent-graft retainment system having a retainer structure, and a retainer release trigger coupled to the retainer structure, the retainer release trigger including a trigger portion extending radially from the lumen through the trigger aperture; and a sheath having a trigger trip surface.

In yet another embodiment according to the present invention, a stent-graft retainment system includes: a retainer structure; and a retainer release trigger coupled to the retainer structure, the retainer release trigger having a pull rod portion coupled to a trigger portion.

The present invention is best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 2:
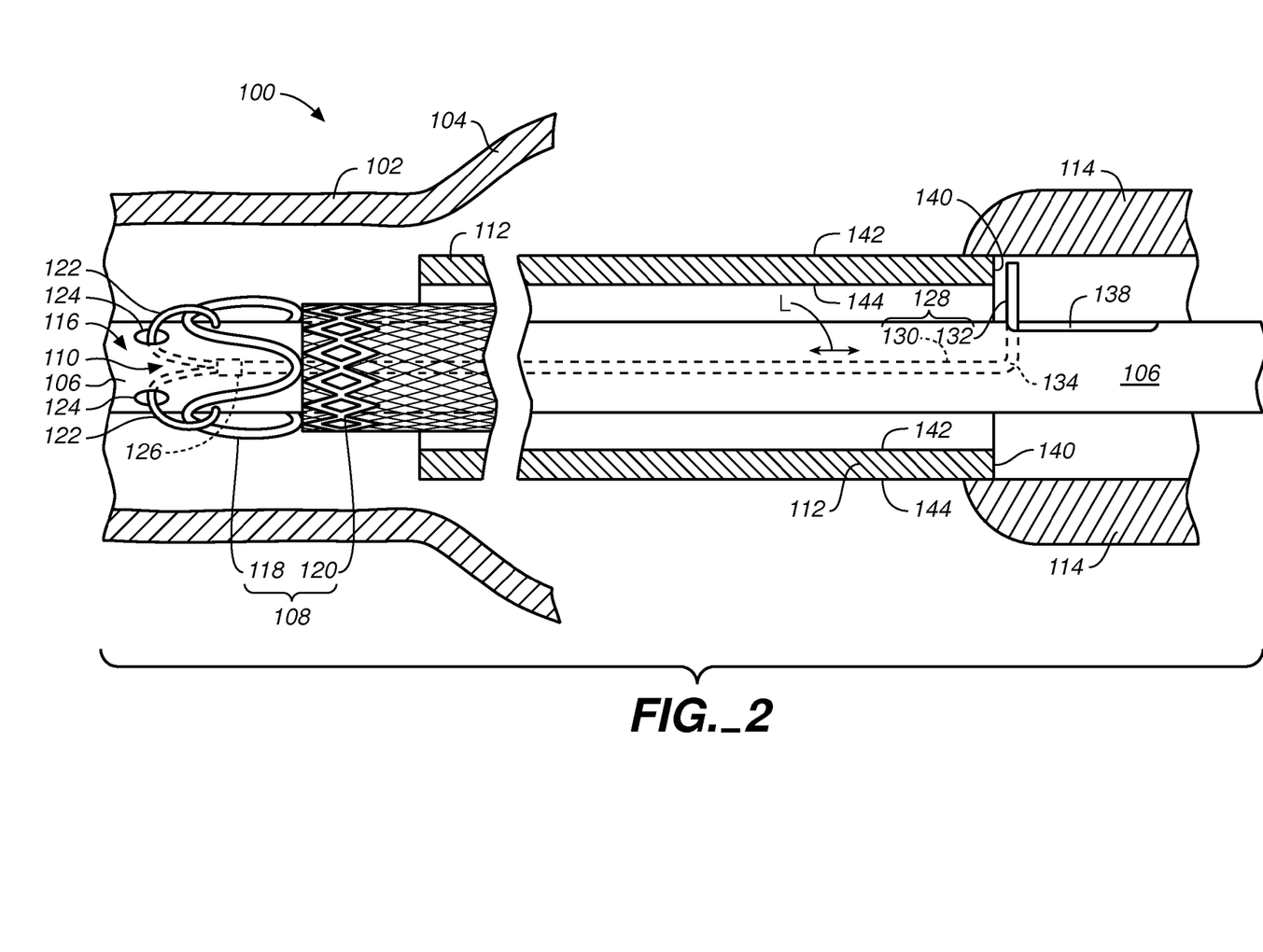
FIG. 2 is a modified partial cross-section view of the stent-graft delivery system of FIG. 1 during deployment of the stent-graft.
Figure 3:
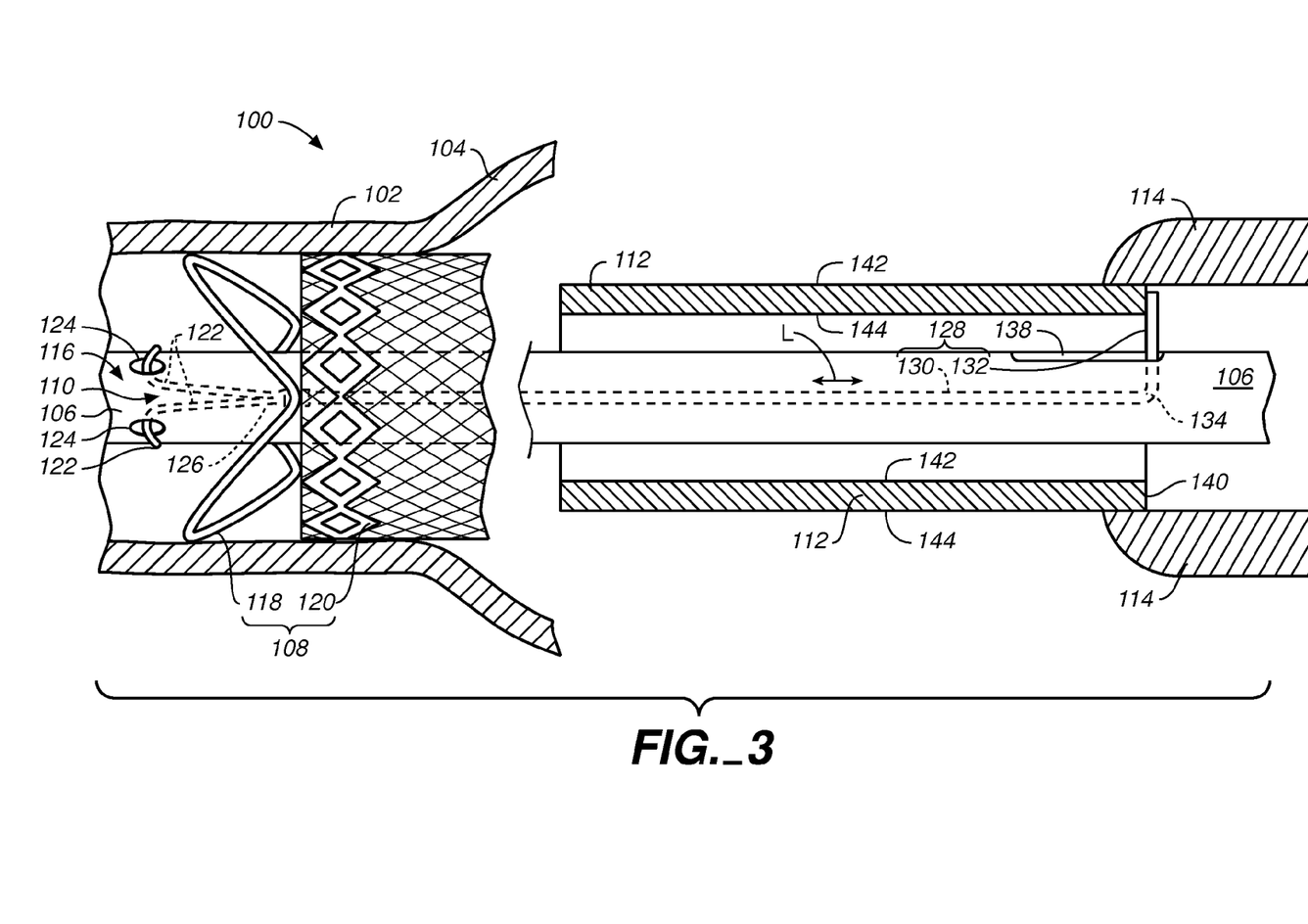
FIG. 3 is a modified partial cross-section view of the stent-graft delivery system of FIG. 2 at a further stage during deployment of the stent-graft.

In one embodiment according to the present invention, a method of delivering a stent-graft 108 includes mounting stent-graft 108 on a pushrod 106 (FIG. 1); radially constraining stent-graft 108 within a sheath 112; securing a crown portion 118 of stent-graft 108 to pushrod 106 with a retainer structure 122 of a stent-graft retainment system 110; retracting sheath 112 to expose crown portion 118 of stent-graft 108 (FIG. 2); and further retracting sheath 112 to cause retainer structure 122 to release crown portion 118 from pushrod 106 thus deploying stent-graft 108 (FIG. 3).

Retainer structure 122 releases stent-graft 108 automatically as a result of the retraction of sheath 112. Thus, exposure of crown portion 118 by sheath 112 (FIG. 2) followed by release of crown portion 118 by retainer structure 122 (FIG. 3) does not require any additional manipulations by the physician compared to a conventional stent-graft delivery system.

Figure 1:
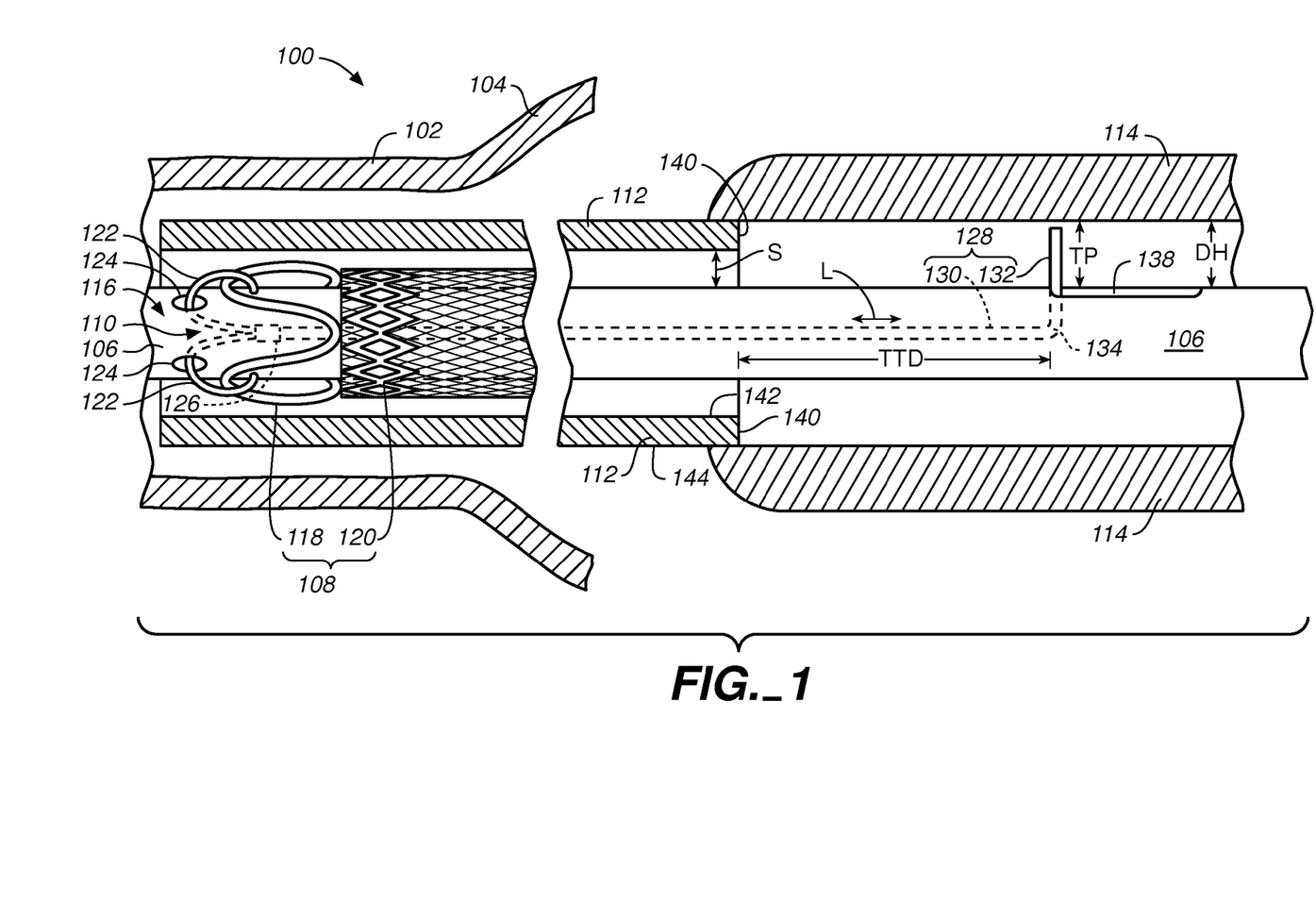
FIG. 1 is a modified partial cross-section view of a stent-graft delivery system within a parent vessel of a patient adjacent to a fistula aneurysm.

More particularly, FIG. 1 is a modified partial cross-section view of a stent-graft delivery system 100 within a parent vessel 102 of a patient adjacent to a fistula aneurysm 104. Illustratively, fistula aneurysm 104 is an intra-cranial or aortic aneurysm although other aneurysms are treated in other embodiments.

Delivery system 100 includes a pushrod 106, a stent-graft 108, a stent-graft retainment system 110, a sheath 112, and a delivery handle 114.

In accordance with this embodiment, pushrod 106, sometimes called an inner catheter, is a hollow tubular member and includes a lumen 116, e.g., a guide wire lumen. In one embodiment (not shown), pushrod 106 includes an expandable catheter balloon for expanding and anchoring stent-graft 108 within parent vessel 102 as those of skill in the art will understand in light of this disclosure. However, for purposes of simplicity, stent-graft 108 is discussed below as being a self-expanding stent-graft.

Stent-graft 108 is placed over and mounted on pushrod 106. In one embodiment, pushrod 106 and/or stent-graft 108 include radiopaque markers, which allow the location of stent-graft 108 to be precisely tracked facilitating positioning of stent-graft 108 within parent vessel 102.

Stent-graft 108 is radially constrained by sheath 112. More particularly, prior to deployment, stent-graft 108 is located within sheath 112. Sheath 112 is coupled, e.g., with adhesive, to delivery handle 114.

Stent-graft 108 includes a crown portion 118, sometimes called a bare stent portion, at a proximal (upstream) end (with respect to an aortic deployment) of stent-graft 108. Stent-graft 108 further includes a stent-graft portion 120 coupled to crown portion 118.

Crown portion 118 of stent-graft 108 is secured to pushrod 106 by stent-graft retainment system 110. More particularly, crown portion 118 of stent-graft 108 is secured to pushrod 106 by a retainer structure 122, sometimes called a retainment means or means for retaining, of stent-graft retainment system 110.

Retainer structure 122 is a plurality of curved wires, sometimes called hooks, extending from lumen 116 through corresponding retainer apertures 124 of pushrod 106. Generally, retainer structure 122 includes at least one curved wire. Retainer structure 122 is formed of a rigid material, e.g., steel or spring steel, having a sufficient rigidity and strength to hold crown portion 118 of stent-graft 108 in place.

The plurality, e.g., two or more, of curved wires of retainer structure 122 are connected together by a trigger wire coupler 126 of stent-graft retainment system 110 at a proximal (downstream) end of retainer structure 122. The plurality of curved wires of retainer structure 122 extend distally (upstream) and outwards from trigger wire coupler 126. The plurality of curved wires of retainer structure 122 pass out from lumen 116 through corresponding retainer apertures 124 of pushrod 106 and curve to extend over crown portion 118 and back in the proximal (downstream) direction. However, in another embodiment (not shown), the plurality of wires of retainer structure 122 pass out from lumen 116 proximally (downstream) of crown portion 118 and extend over crown portion 118 in the distal (upstream) direction.

Stent-graft retainment system 110 further includes a retainer release trigger 128 coupled to retainer structure 122 by trigger wire coupler 126. Retainer release trigger 128, sometimes called a graft release trigger, is formed of a rigid material, e.g., a steel wire, having a sufficient rigidity and strength to cause retraction of retainer structure 122.

Although retainer structure 122 is illustrated and discussed above as being coupled to retainer release trigger 128 by trigger wire coupler 126, in another embodiment, retainer structure 122 and retainer release trigger 128 are integral, i.e., are a single piece not a plurality of separate pieces coupled together.

In the embodiment illustrated in FIG. 1, retainer release trigger 128 comprises a pull rod portion 130 and a trigger portion 132 coupled together at a bend portion 134. In this embodiment, pull rod portion 130, trigger portion 132 and bend portion 134 are integral, but can be separate pieces connected together in another embodiment.

A distal (upstream) end of pull rod portion 130 is coupled to trigger wire coupler 126. Pull rod portion 130 extends longitudinally in the proximal direction from trigger wire coupler 126 through lumen 116 of pushrod 106. Pull rod portion 130 is coupled to trigger portion 132 at a proximal (downstream) end of pull rod portion 130.

Generally, pull rod portion 130 extends along the length of longitudinal axis L of pushrod 106 and thus pull rod portion 130 is sometimes said to extend longitudinally or in the longitudinal direction. Trigger portion 132 extends in a direction perpendicular to longitudinal axis L of pushrod 106 and thus trigger portion 132 is sometimes said to extend radially or in the radial direction. Bend portion 134 bends from the longitudinal direction to the radial direction.

Pushrod 106 further comprises a trigger aperture 138. In this embodiment, trigger aperture 138 is a longitudinal slot in pushrod 106. Trigger portion 132 extends radially from lumen 116 of pushrod 106 and through trigger aperture 138. Trigger portion 132 extends radially outwards from pushrod 106 a radial distance TP, sometimes called a first radial distance. The radial distance S, sometimes called a second radial distance, between sheath 112 and pushrod 106 is less than the distance TP of trigger portion 132. Thus, sheath 112 contacts trigger portion 132 during retraction. Pull rod portion 130 is positioned within pushrod 106, for example, by splitting and rejoining the radial sections of pushrod 106. A separate lumen within pushrod 106 guides the motion of pull rod portion 130 in one embodiment.

However, to prevent trigger portion 132 from contacting delivery handle 114, the radial distance DH, sometimes called a third radial distance, between delivery handle 114 and pushrod 106 is greater than the distance TP of trigger portion 132. This allows delivery handle 114 to be moved without contacting trigger portion 132 as discussed in greater detail below.

More particularly, sheath 112 comprises an annular trigger trip surface 140, which is perpendicular to longitudinal axis L of pushrod 106. Trigger trip surface 140 is located at the proximal (downstream) end of sheath 112 and extends between an inner surface 142 and an outer surface 144 of sheath 112. Prior to retraction of sheath 112, a longitudinal trigger trip distance TTD exists between trigger trip surface 140 and trigger portion 132. Although trigger trip surface 140 is discussed and illustrated herein as being a surface of sheath 112, in an alternative embodiment (not shown), trigger trip surface 140 is a surface of a different element of delivery system 100, e.g., of delivery handle 114.

FIG. 2 is a modified partial cross-section view of stent-graft delivery system 100 during deployment of stent-graft 108. Referring now to FIGS. 1 and 2 together, to deploy stent-graft 108, delivery handle 114 is retracted. Since sheath 112 is coupled to delivery handle 114, retraction of delivery handle 114 causes retraction of sheath 112.

Since retainer structure 122 holds crown portion 118 against pushrod 106, the large normal force which would otherwise be exerted by crown portion 118 of stent-graft 108 against inner surface 142 of sheath 112 is minimized. Since the normal force is minimized, graft-to-sheath friction is minimized thus minimizing the deployment force, i.e., the force exerted upon delivery handle 114 during retraction. In addition, a reduction in the normal force minimizes any embedding (mechanical engagement) of stent-graft 108 into sheath 112, which further minimizes the deployment force.

By minimizing the deployment force, the stress on stent-graft 108 is minimized thus minimizing the possibility of damaging stent-graft 108 during deployment. Further, by minimizing the deployment force, the stress on delivery system 100 is minimized thus also minimizing the possibility of damaging delivery system 100 during deployment of stent-graft 108. For example, stretching of sheath 112 and the associated possibility of necking of sheath 112 (diameter reduction) and/or failures at bonds between components, e.g., between sheath 112 and delivery handle 114, are minimized by minimizing the deployment force.

Further, stent-graft 108 is placed in tension rather than compression during deployment. More particularly, stent graft 108 is pulled proximally (downstream) from crown portion 118 and retainer structure 122 by sheath 112 during deployment. This minimizes the possibility of bunching of stent-graft 108.

After delivery handle 114 and the sheath 112 are retracted, i.e., moved, trigger trip distance TTD, sheath 112 contacts trigger portion 132 as shown in FIG. 2. More particularly, trigger trip surface 140 contacts trigger portion 132 and thus further retraction of delivery handle 114 and sheath 112 causes an equal retraction of trigger portion 132.

FIG. 3 is a modified partial cross-section view of stent-graft delivery system 100 of FIG. 2 at a further stage during deployment of stent-graft 108. Referring now to FIGS. 2 and 3 together, further retraction of delivery handle 114 and sheath 112 causes retraction of trigger portion 132 and release of crown portion 118 of stent-graft 108.

More particularly, retraction of trigger portion 132 causes proximal (downstream towards delivery handle 114) longitudinal motion of pull rod portion 130. This, in turn, causes proximal longitudinal motion of trigger wire coupler 126 and retraction of the plurality of curved wires of retainer structure 122, i.e., causes retraction of retainer structure 122, into pushrod 106.

As retainer structure 122 is retracted to expose crown portion 118, crown portion 118 is released from pushrod 106 by retainer structure 122. Since sheath 112 has also been retracted to expose crown portion 118, crown portion 118 self-expands into contact with parent vessel 102. Further retraction of delivery handle 114 and sheath 112 completes deployment of stent-graft 108.

As discussed above, retainer structure 122 releases stent-graft 108 automatically during retraction of delivery handle 114. Thus, use of stent-graft delivery system 100 including stent-graft retainment system 110 does not require any additional operations (manipulation) by the physician compared to a conventional stent-graft delivery system.

Further, referring again to FIG. 1, trigger trip distance TTD controls how much of stent-graft 108 is exposed by sheath 112 prior to release by retainer structure 122. Accordingly, by appropriately defining trigger trip distance TTD, stent-graft 108 is released after a desired amount of stent-graft 108 is exposed by sheath 112.

For example, stent-graft 108 is released after sheath 112 has uncovered and exposed the first few stent rings, e.g., crown portion 118 and the most proximal 2 to 4 stent rings, of stent-graft 108. Crown portion 118 and the first few stent rings of stent-graft 108 cause the highest normal friction and associated deployment force. Thus, by restraining crown portion 118 against pushrod 106 by retainer structure 122 during retraction of sheath 112 over the first few stent rings, a significant benefit is obtained. Further, this allows the physician to uncover the first stent rings and assess the position of stent-graft 108 in parent vessel 102 before releasing crown portion 118 and sealing the stent-graft 108 in parent vessel 102.

Figure 4:
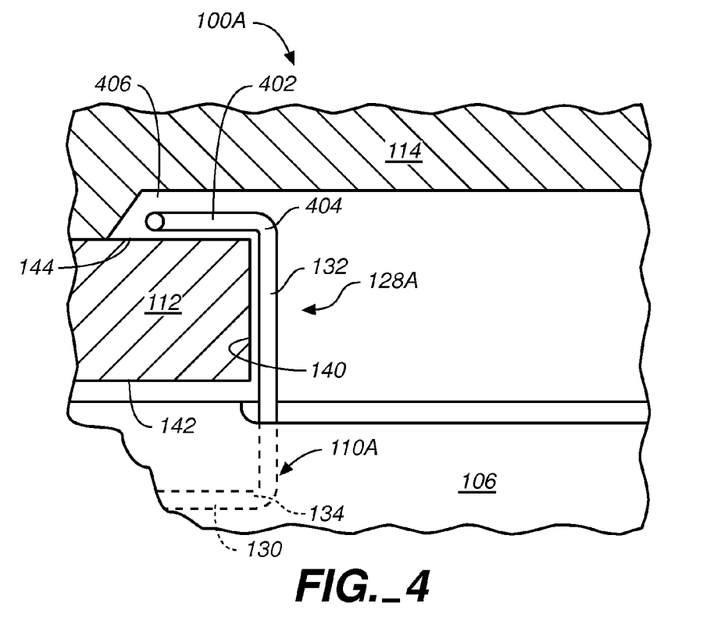
FIG. 4 is a modified partial cross-section view of a region of a stent-graft delivery system.

FIG. 4 is a modified partial cross-section view of a region of a stent-graft delivery system 100A of another embodiment according to the present invention. Retainer release trigger 128A of stent-graft retainment system 110A of stent-graft delivery system 100A includes a locking feature 402, sometimes called a locking means, for securing trigger portion 132 to sheath 112.

More particularly, locking feature 402 and trigger portion 132 are coupled together at a bend portion 404. In this configuration, trigger portion 132, locking feature 402, and bend portion 404 are integral, but can be separate pieces connected together in another embodiment.

A proximal (downstream) end of locking feature 402 is coupled to trigger portion 132 by bend portion 404. Locking feature 402 extends in the distal (upstream) direction from trigger portion 132.

When trigger portion 132 is engaged with trigger trip surface 140 of sheath 112 as illustrated in FIG. 4, locking feature 402 is adjacent to outer surface 144 of sheath 112. This locks retainer release trigger 128A around the proximal end of sheath 112 thus ensuring that retainer release trigger 128A does not slip from sheath 112. Delivery handle 114 is configured to accommodate the positioning of locking feature 402, e.g., by providing a space 406 between delivery handle 114 and outer surface 144 of sheath 112.

Figure 5:
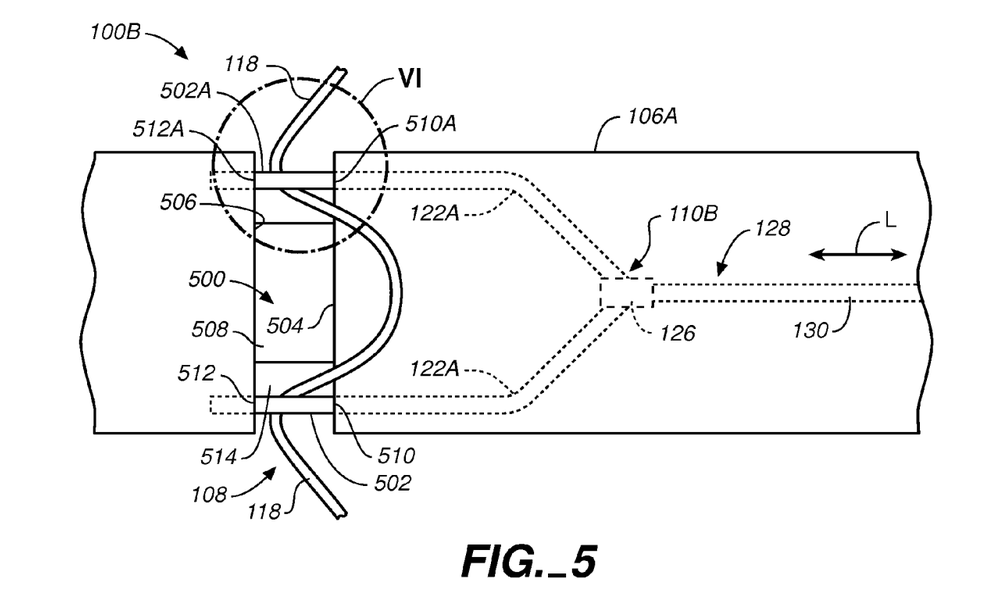
FIG. 5 is a partial side view of a stent-graft delivery system having a crown portion of a stent-graft engaged with a stent-graft retainment system.
Figure 6:
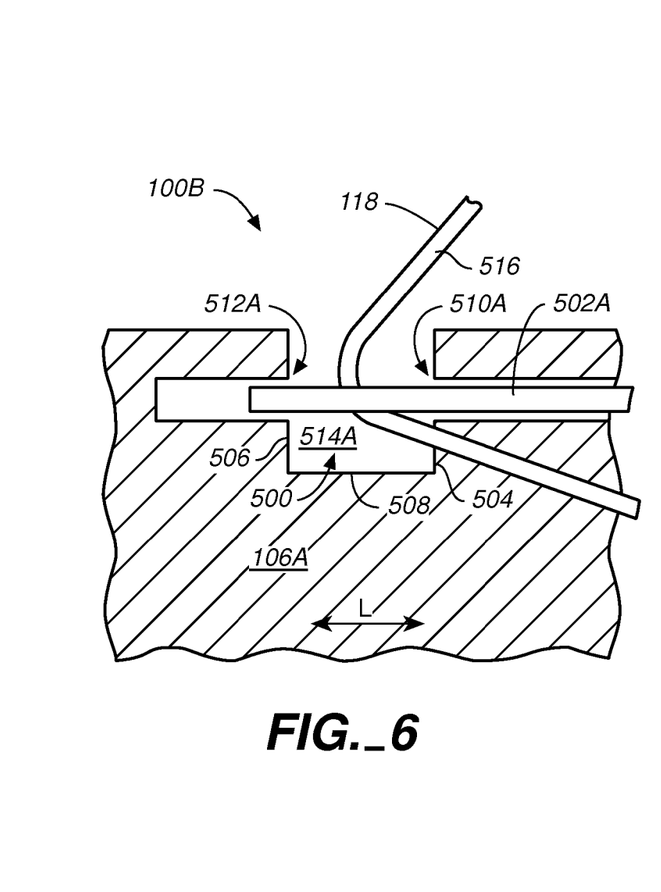
FIG. 6 is a side partial cross-section view of a region VI of the delivery system of FIG. 5.

FIG. 5 is a partial side view of a stent-graft delivery system 100B having crown portion 118 of stent-graft 108 engaged with a stent-graft retainment system 110B of another embodiment according to the present invention. Delivery system 100B is similar to delivery system 100 of FIGS. 1, 2, and 3 and so various elements, e.g., sheath 112, are not illustrated in FIG. 5. FIG. 6 is a side partial cross-section view of a region VI of delivery system 100B of FIG. 5.

Referring now to FIGS. 5 and 6 together, pushrod 106A comprises at least one trench 500 extending partially or completely around the circumference of pushrod 106A. Further, a retainer structure 122A comprises straight wires 502 (only a wire 502 and a wire 502A of the plurality of wires 502 are illustrated in FIG. 5) extending across trench 500 of pushrod 106A. Generally, retainer structure 122A includes at least one wire 502.

More particularly, trench 500 is defined by a proximal (partial or full) annular surface 504, e.g., at least one proximal annular surface, a distal (partial or full) annular surface 506, e.g., at least one distal annular surface, and a longitudinal (partial or full) ring surface 508, e.g., at least one longitudinal ring surface. In this embodiment, proximal annular surface 504 and distal annular surface 506 are perpendicular to longitudinal axis L of pushrod 106A. Further, longitudinal ring surface 508 is parallel to longitudinal axis L of pushrod 106A.

Proximal annular surface 504 and distal annular surface 506 includes proximal retainer apertures 510 (only a proximal retainer aperture 510 and a proximal retainer aperture 510A of the plurality of proximal retainer apertures 510 are illustrated in FIG. 5) and corresponding distal retainer apertures 512 (only a distal retainer aperture 512 and a distal retainer aperture 512A of the plurality of distal retainer apertures 512 are illustrated in FIG. 5), respectively. Wires 502 extend distally from pushrod 106A through proximal retainer apertures 510, longitudinally across trench 500, and back into pushrod 106A through distal retainer apertures 512.

To illustrate, a first wire 502A of the plurality of wires 502 extends distally from pushrod 106A through a first proximal retainer aperture 510A of the plurality of proximal retainer apertures 510, longitudinally across trench 500, and back into pushrod 106A through a first distal retainer aperture 512A of the plurality of distal retainer apertures 512 as shown in FIGS. 5 and 6.

Figure 7:
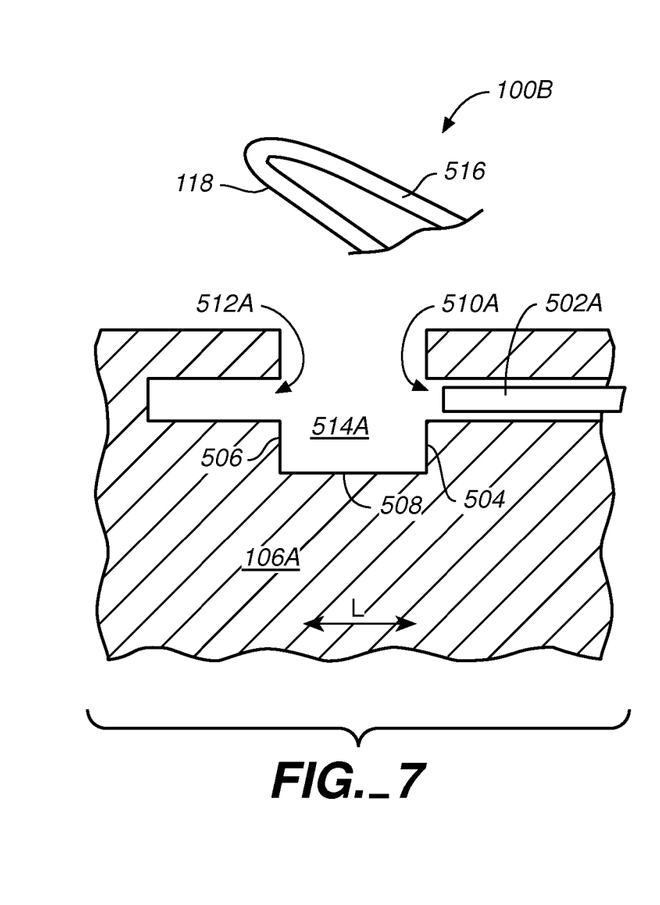
FIG. 7 is a side partial cross-section view of the region VI of the delivery system of FIG. 6 during deployment of the stent-graft.

FIG. 7 is a side partial cross-section view of region VI of delivery system 100B of FIG. 6 during deployment of stent-graft 108.

Referring now to FIGS. 5, 6, and 7 together, proximal annular surface 504, distal annular surface 506, longitudinal ring surface 508 and wires 502 define pockets 514 (only a pocket 514 and a pocket 514A of the plurality of pockets 514 are illustrated in FIGS. 5, 6, 7). Prior to deployment of stent-graft 108, crown portion 118 is retained within pockets 514.

To illustrate, proximal annular surface 504, distal annular surface 506, longitudinal ring surface 508 and wire 502A define a first pocket 514A of the plurality of pockets 514. A loop 516 of crown portion 118 passes through pocket 514A and presses radially outwards on wire 502A.

To deploy stent-graft 108, trigger wire coupler 126 is retracted as discussed above in reference to FIGS. 2 and 3. This causes retraction of wires 502 of retainer structure 122A. More particularly, wires 502 are retracted out of distal retainer apertures 512 and into proximal retainer apertures 510. Stated another way, wires 502 are retracted thus opening pockets 514. This releases crown portion 118 of stent-graft 108 resulting in deployment of stent-graft 108 as shown in FIG. 7.

Figure 8:
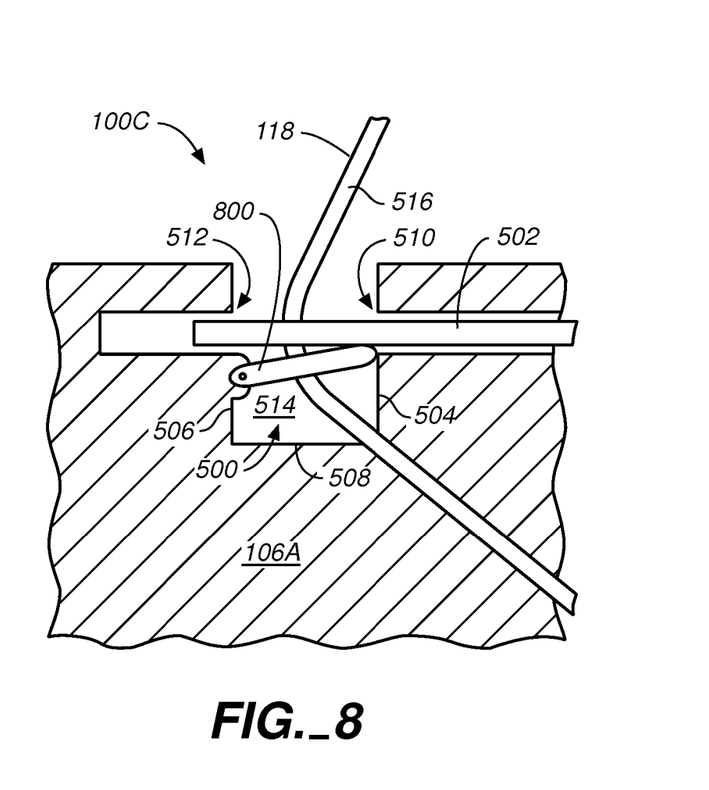
FIGS. 8 and 9 are side partial cross-section views of a region of a stent-graft delivery system during deployment of a stent-graft.
Figure 9:
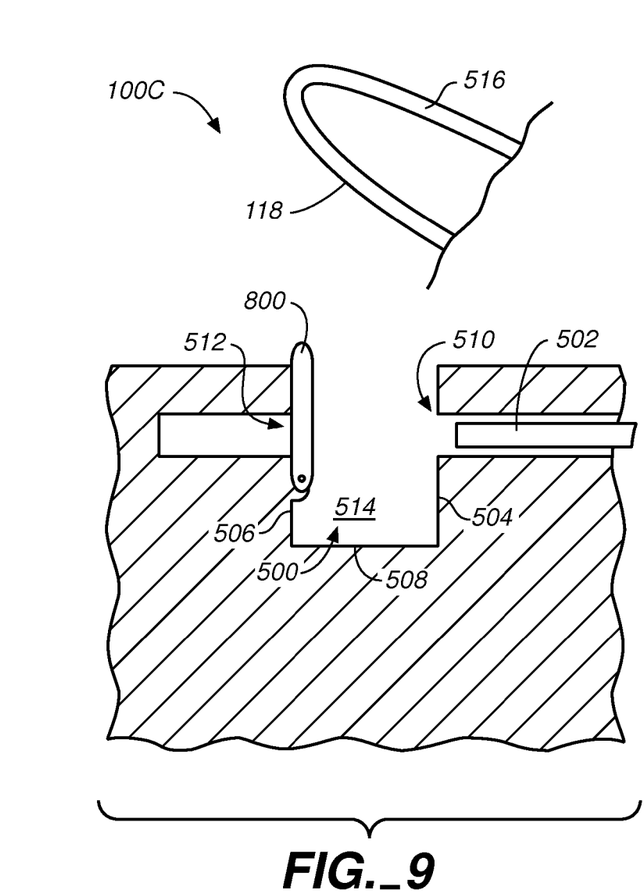

In another embodiment, direct contact between crown portion 118 and retractable wires 502 is avoided. FIGS. 8 and 9 are side partial cross-section views of a region of a stent-graft delivery system 100C during deployment of stent-graft 108 according to another embodiment of the present invention.

Referring now to FIGS. 8 and 9 together, swings 800 are pivotally attached to distal annular surface 506 and extend across localized portions of trench 500. The number of swings 800 corresponds to the number of wires 502 around pushrod 106A. As shown in FIG. 8, crown portion 118 presses upon swings 800 which, in turn, press upon wires 502.

To deploy stent-graft 108, wires 502 are retracted as discussed above. More particularly, wires 502 are retracted out of distal retainer apertures 512 and into proximal retainer apertures 510. Stated another way, wires 502 are retracted thus opening pockets 514. This releases swings 800, which pivot from distal annular surface 506. This, in turn, releases crown portion 118 of stent-graft 108 resulting in deployment of stent-graft 108 as shown in FIG. 9.

In one embodiment, the coefficient of friction between swings 800 and wires 502 is less than the coefficient of friction between crown portion 118 and wires 502. Accordingly, use of swings 800 minimizes deployment force.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method comprising:
   mounting a stent-graft on a pushrod;
   radially constraining said stent-graft within a sheath;
   securing a crown portion of said stent-graft to said pushrod with a retainer structure of a stent-graft retainment system;
   retracting said sheath to expose said crown portion of said stent-graft such that said crown portion is not constrained within said sheath, wherein said crown portion remains secured to said pushrod after said crown portion is exposed; and
   further retracting said sheath to release said crown portion from said retainer structure and said pushrod.

2. The method of claim 1 wherein said stent-graft self-expands upon said release of said crown portion from said pushrod.

3. The method of claim 1 wherein said step of further retracting said sheath comprises a trigger trip surface of said sheath contacting a trigger portion of said stent-graft retainment system.

4. The method of claim 3 wherein said step of further retracting said sheath further comprises said trigger trip surface retracting said trigger portion to retract said retainer structure.

5. The method of claim 4 wherein said retainer structure is retracted to release said crown portion from said retainer structure.

6. The method of claim 3 wherein a locking feature is coupled to said trigger portion such that when said trigger trip surface contacts said trigger portion, said locking feature extends longitudinally outside of said sheath.

* * * * *